United States Patent
Thomas

[19]

[11] Patent Number: 6,153,148
[45] Date of Patent: Nov. 28, 2000

[54] CENTRIFUGAL HEMATOLOGY DISPOSABLE

[75] Inventor: Bradley S. Thomas, Timonium, Md.

[73] Assignee: Becton, Dickinson and Company, Franklin Lakes, N.J.

[21] Appl. No.: 09/097,475

[22] Filed: Jun. 15, 1998

[51] Int. Cl.⁷ ..................................................... G01N 9/30

[52] U.S. Cl. ............................. 422/72; 422/68.1; 422/73; 422/101; 422/102; 436/45; 436/164; 436/165; 436/177

[58] Field of Search ................................ 422/68.1, 72, 73, 422/101, 102; 436/45, 164, 165, 177, 180

[56] References Cited

U.S. PATENT DOCUMENTS

| | | | |
|---|---|---|---|
| 3,508,878 | 4/1970 | Gunders | 23/253 |
| 4,027,660 | 6/1977 | Wardlaw et al. . | |
| 4,077,396 | 3/1978 | Wardlaw et al. . | |
| 4,082,085 | 4/1978 | Wardlaw et al. | 128/2 G |
| 4,156,570 | 5/1979 | Wardlaw . | |
| 4,284,602 | 8/1981 | Kelton et al. | 422/72 |
| 4,558,947 | 12/1985 | Wardlaw . | |
| 4,567,754 | 2/1986 | Wardlaw et al. . | |
| 4,580,897 | 4/1986 | Nelson et al. | 356/246 |
| 4,623,519 | 11/1986 | Cornut et al. . | |
| 4,735,502 | 4/1988 | Kaufmann . | |
| 4,823,624 | 4/1989 | Rodriguez et al. . | |
| 4,963,498 | 10/1990 | Hillman et al. | 436/69 |
| 5,061,381 | 10/1991 | Burd | 210/789 |
| 5,061,446 | 10/1991 | Guigan . | |
| 5,256,376 | 10/1993 | Callan et al. | 422/102 |
| 5,518,930 | 5/1996 | Burd | 436/45 |
| 5,534,226 | 7/1996 | Gavin et al. | 422/73 |
| 5,639,428 | 6/1997 | Cottingham | 422/112 |
| 5,696,233 | 12/1997 | Schembri | 210/787 |
| 5,814,279 | 9/1998 | Biesel et al. | 422/72 |

OTHER PUBLICATIONS

QBC® Autoread™ Plus Brochure, Becton Dickinson and Company, 1996.

*Primary Examiner*—Jill Warden
*Assistant Examiner*—Kathryn Bex
*Attorney, Agent, or Firm*—Bruce S. Weintraub, Esq.

[57] ABSTRACT

A shatter-proof fluid sample container adaptable for use with a centrifuge is provided. The fluid sample container is especially useful for expanding layers of a fluid sample, such as a blood sample, that form during centrifugation. The fluid sample container includes at least one fill well, a reagent pellet well including a reagent pellet containing reagents and dyes, a mixing channel, a distribution cavity which distributes the fluid to a plurality of expansion cavities, and a float cavity which includes a constant density precision molded float. As the fluid is centrifuged in the fluid sample container, the fluid contacts and dissolves the reagent pellet, and flows through the mixing channel where the material in the reagent pellet mixes with the fluid. The fluid collects in a distribution cavity until the rotational speed of the centrifuge is increased to impose a centrifugal force on the fluid sufficient to cause the fluid to flow over a ramped portion separating the distribution cavity from the plurality of expansion cavities and the float cavity. The expansion cavities each include a portion having a cross-sectional area smaller than the cross-sectional area of any other portion of the expansion cavity. The area having the smaller cross-sectional area has the effect of expanding certain component layers formed in the centrifuged sample, thus making the boundaries of those component layers, such as the buffy coat layers in a blood sample, more readily ascertainable and thus easier to read with an optical reader. The float cavity contains a float having a controlled density such that it centers itself on the buffy coat region when the blood cells are packed by centrifugal force. The depth of float penetration into the packed red blood cells is a function of the RBC density. Since the RBC density is proportional to hemoglobin concentration, the instrument can calculate % Hg from float depth.

13 Claims, 11 Drawing Sheets

CENTRIFUGAL HEMATOLOGY DISPOSABLE

BACKGROUND OF THE INVENTION

1. Field of the Invention

The present invention relates generally to a container for holding a fluid sample to be centrifuged. More particularly, the present invention relates to a container having a plurality of fluid expansion cavities which expand the length of different density layers in the centrifuged sample so that the boundaries of certain density layers are more readily ascertainable.

2. Description of the Related Art

As part of a routine physical or diagnostic examination of a patient, it is common for a physician to order a complete blood count for the patient. The patient's blood sample may be collected in one of two ways. In the venous method, a syringe is used to collect a sample of the patient's blood in a test tube containing an anticoagulation agent. A portion of the sample is later transferred to a narrow glass sample tube such as a capillary tube. The open end of the sample tube is placed in the blood sample in the test tube, and a quantity of blood enters the sample tube by capillary action. The sample tube has two fill lines at locations along its length, and the volume of blood collected should reach a level in the sample tube between the two fill lines. In the capillary method, the syringe and test tube are not used, and the patient's blood is introduced directly into the sample tube from a small incision made in the skin. In either case, the sample tube is then placed in a centrifuge, such as the Model 424740 centrifuge manufactured by Becton Dickinson and Company.

In the centrifuge, the sample tube containing the blood sample is rotated at a desired speed (typically 8,000 to 12,000 rpm) for several minutes. The high speed centrifugation separates the components of the blood by density. Specifically, the blood sample is divided into a layer of red blood cells, a buffy coat region consisting of layers of granulocytes, mixed lymphocytes and monocytes, and platelets, and a plasma layer. The length of each layer can then be optically measured, either manually or automatically, to obtain a count for each blood component in the blood sample. This is possible because the inner diameter of the sample tube and the packing density of each blood component is known, and hence the volume occupied by each layer and the number of cells contained within it can be calculated based on the measured length of the layer. Exemplary measuring devices that can be used for this purpose include those described in U.S. Pat. Nos. 4,156,570 and 4,558,947, both to Stephen C. Wardlaw, and the QBC® "AUTOREAD" system manufactured by Becton Dickinson and Company.

Several techniques have been developed for increasing the accuracy with which the various layer thickness in the centrifuged blood sample can be determined. For example, because the buffy coat region is typically small in comparison to the red blood cell and plasma regions, it is desirable to expand the length of the buffy coat region so that more accurate measurements of the layers in that region can be made. As described in U.S. Pat. Nos. 4,027,660, 4,077,396, 4,082,085 and 4,567,754, all to Stephen C. Wardlaw, and in U.S. Pat. No. 4,823,624, to Rodolfo R. Rodriguez et al., this can be achieved by inserting a precision-molded plastic float into the blood sample in the sample tube prior to centrifugation. The float has approximately the same density as the cells in the buffy coat region, and thus becomes suspended in that region after centrifugation. Since the outer diameter of the float is only slightly less than the inner diameter of the sample tube (typically by about 80 µm), the length of the buffy coat region will expand to make up for the significant reduction in the effective diameter of the tube that the buffy coat region can occupy due to the presence of the float. By this method, an expansion of the length of the buffy coat region by a factor between 4 and 20 can be obtained. The cell counts calculated for the components of the buffy coat region will take into account the expansion factor attributable to the float.

Another technique that is used to enhance the accuracy of the layer thickness measurements is the introduction of reagents, such as heparin, EDTA anticoagulant coating, potassium oxalate, and monoclonal antibody, and a fluorescent dye such as acridine orange, into the sample tube in the form of dried coatings. When the blood sample is added to the sample tube, these reagents dissolve into the sample. The reagents prevent the blood sample from coagulating, while the dye causes the various blood cell layers to fluoresce at different optical wavelengths when they are excited by a suitable light source. As a result, the boundaries between the layers can be discerned more easily when the layer thicknesses are measured following centrifugation.

Typically, the centrifugation step and the layer thickness measurement step are carried out at different times and in different devices. That is, the centrifugation operation is first carried out to completion in a centrifuge, and the sample tube is then removed from the centrifuge and placed in a separate reading device so that the blood cell layer thicknesses can be measured. More recently, however, a technique has been developed in which the layer thicknesses are calculated using a dynamic or predictive method while centrifugation is taking place. This is advantageous not only in reducing the total amount of time required for a complete blood count to be obtained, but also in allowing the entire procedure to be carried out in a single device. Apparatus and methods for implementing this technique are disclosed in copending U.S. patent applications of Stephen C. Wardlaw entitled "Assembly for Rapid Measurement of Cell Layers", Ser. No. 08/814,536 and "Method for Rapid Measurement of Cell Layers", Ser. No. 08/814,535, both filed on Mar. 10, 1997.

In order to allow the centrifugation and layer thickness steps to be carried out simultaneously, it is necessary to freeze the image of the sample tube as it is rotating at high speed on the centrifuge rotor. This can be accomplished by means of a xenon flash lamp assembly that produces, via a lens and a bandpass filter, an intense excitation pulse of blue light energy (at approximately 470 nanometers) once per revolution of the centrifuge rotor. The pulse of blue light excites the dyes in the expanded buffy coat area of the sample tube, causing the dyes to fluoresce with light of a known wavelength. The emitted fluorescent light resulting from the excitation flash is focused by a high-resolution lens onto a linear CCD array. The CCD array is located behind an array of bandpass filters which selects the specific wavelengths of emitted light to be imaged onto the CCD array.

The xenon flash lamp assembly is one of two illumination sources that are focused onto the sample tube while the centrifuge rotor is in motion. The other source is an array of light-emitting diodes (LEDs) which transmits red light through the sample tube for detection by the CCD array through one of the band pass filters. The purpose of the transmitted light is to initially locate the beginning and end of the plastic float (which indicates the location of the expanded buffy coat area), and the fill lines.

A centrifuge device of the type described above, which includes a flash lamp and a CCD array reader, is further described in a copending U.S. patent application of Bradley S. Thomas entitled "Flash Tube Reflector With Arc Guide", Ser. No. 09/032,935, in a copending U.S. patent application of Michael R. Walters entitled "Inertial Tube Indexer and Method for Using the Same", Ser. No. 09/032,931, in a copending U.S. patent application of Michael A. Kelley, Edward G. King, Bradley S. Thomas and Michael R. Walters entitled "Disposable Blood tube Holder and Method for Using the Same", Ser. No. 09/033,373, and in a copending U.S. patent application of Bradley S. Thomas, Michael A. Kelley, Michael R. Walters, Edward M. Skevington and Paul F. Gaidis entitled "Blood Centrifugation Device With Movable Optical Reader", Ser. No. 09/033,368, all filed on Mar. 2, 1998.

Several problems exist with using a standard sample tube in a centrifugation device of the type described above. In particular, because the tube is made of glass, it is possible for the tube to shatter either during handling or during centrifugation if the tube is not properly handled or loaded. If this occurs, the blood sample in the tube can come in contact with the person handling the tube, or can become an aerosol if the tube is being centrifuged. Therefore, any pathogen that may be present in the blood sample can be spread to people in the immediate area of the centrifuge device. Also, the shattered tube can result in injury due to sharp edges or flying glass.

Furthermore, in conventional centrifuging methods, the sample tube is not sealed prior to centrifugation. Hence, infectious agents that may exist in the blood sample can possibly become airborne during centrifugation even if the tube does not break.

Although it is possible to coat the sample tube with a shatterproofing material, this drastically increases the cost of the sample tube while only slightly improving safety. Furthermore, this technique does not positively isolate the blood sample in the tube from the outside atmosphere. As a result, some of the blood sample can still escape during centrifugation.

Consideration has also been given to manufacturing the sample tube from a shatterproof material, such as plastic. However, this proposed solution is unsatisfactory for several reasons. For example, although plastic extrusion methods are known for manufacturing plastic tubes, the known methods do not consistently provide a plastic tube having an inner diameter within the tolerance needed to obtain accurate buffy coat region measurements. That is, for the buffy coat measurements to be accurate, the inner diameter of the sample tube must not vary from the desired magnitude by more than 0.0003 inches. Although this close tolerance can be obtained when manufacturing glass sample tubes, the plastic extrusion method is incapable of maintaining this tolerance.

As an alternative to the plastic extrusion method, a plastic sample tube could be made by an injection molding process as known in the art. However, known injection molding processes create a taper or "draft" in the tube which adversely affects measurements of the buffy coat region in the fluid sample. Hence, plastic tubes manufactured by an injection molding process are also impractical for blood analysis applications of the type described above.

Other problems also exist with the known sample tubes including a float as described above. For example, when a float is inserted into a sample tube containing a blood sample, the float typically sinks to the bottom of the blood sample. As the sample is centrifuged, the float begins to migrate within the blood sample as the layers of the blood components are being formed, and becomes suspended in the centrifuged blood sample at a level governed by the density of the float with respect to the density of the blood sample component layers in the centrifuged blood sample. As the float migrates through the layers of the buffy coat region toward its final location in the blood sample, the float forces its way through the cell layers. When this occurs, some of the cells may be squeezed between the outer diameter of the float and the inner diameter of the sample tube, become damaged, and adhere to the inner diameter of the sample tube, thus resulting in uneven or wavy cell layers in the buffy coat region.

The float in conventional blood sample tubes also functions to mix the dyes and reagents present in the sample tube with the blood sample when the blood sample is being centrifuged. That is, as the float migrates through the blood sample being centrifuged, the movement of the float agitates the blood sample and thus helps to mix dried coatings of dyes and reagents present in the tube with the blood sample.

Fluid sample containers adaptable for use with a centrifuge are known in the art and are described, for example, in the U.S. Pat. No. 5,639,428 to Cottingham, U.S. Pat. No. 5,256,376 to Callan et al., U.S. Pat. No. 5,061,446 to Guigan, U.S. Pat. No. 4,735,502 to Kaufmann, U.S. Pat. No. 4,623,509 to Cornut et al., and U.S. Pat. No. 4,580,897 to Nelson et al. However, none of these containers are designed to expand the component layers of the centrifuged sample, in particular, a blood sample, to make the boundaries of those layers more readily ascertainable, thus making those layers easier to read with an optical reader.

Accordingly, a continuing need exists for a shatterproof fluid sample container that can be used with a centrifuge and a reading device to centrifuge and examine the component layers of the centrifuged sample, as when performing a complete blood count. A continuing need also exists for a fluid sample container which does not require the use of a float to expand for examination of the buffy coat region that is formed in a blood sample when the blood sample in the container is centrifuged. A continuing need also exists for a fluid sample container which is adaptable for use with a centrifuge and is capable of mixing materials, such as dyes, reagents and the like, with the sample contained therein without the use of a float or other type of mixing device suspended in the fluid.

SUMMARY OF THE INVENTION

An object of the invention is to provide a shatter-proof fluid sample container, which is adaptable for use with a centrifuge and a reading device resident in or remote from the centrifuge, to perform an analysis of a blood sample that is separated into blood component layers by the centrifuge.

Another object of the invention is to provide a shatter-proof fluid sample container, adaptable for use with a centrifuge, which receives a blood sample for centrifugation and expands the buffy coat region of the centrifuged blood sample without using a constant density float.

A still further object of the invention is to provide a fluid sample container which is adaptable for use with a centrifuge and includes channels for mixing with the fluid a material, such as a dye or reagent present in the container, without the need for a float or other device suspended in the fluid sample.

These and other objects of the invention are achieved by providing a container, adaptable for use with a centrifuge, and comprising a fill well section, a channel section, and a fluid expansion cavity section. The fill well section includes a fill well which receives the fluid sample through an opening in the container. The channel section defines a channel system providing communication between the fill well and the fluid expansion cavities. When the container is spun in a centrifuge, the fluid sample received in the fill well begins to flow through the channel system. Material such as reagents and dyes, which are preferably formed in the shape of a pellet, are present in the channel system.

As the fluid flows through the channel system, the fluid contacts and dissolves the pellet. The channel system has, for example, a zig-zag shaped portion which facilitates mixing of the material in the pellet with the fluid as the fluid flows through the channel system. The fluid is then collected in a distribution cavity portion of the channel system, which includes a ramped side that restricts the flow of fluid into the fluid expansion cavities.

Once the speed of rotation of the centrifuge is increased to a certain level, the centrifugal force imposed on the fluid by the centrifuge forces the fluid to spill over the ramped portion of the distribution cavity and into the plurality of fluid expansion cavities. The fluid expansion cavities each include a first portion having a certain cross-sectional area, and a second portion having a cross-sectional area which is a fraction of the cross-sectional area of the first portion. Hence, the smaller cross-sectional area portion expands the width of certain of the component density layers of the fluid which are formed by the centrifuging. If, for example, the sample fluid is a blood sample, the layers of the buffy coat region appear in the smaller cross-sectional area portion of at least one of the fluid expansion cavities, and is thus expanded by this smaller portion. An optical viewer in the centrifuge or separate from the centrifuge can be used to read the buffy coat region.

BRIEF DESCRIPTION OF THE DRAWINGS

These and other objects and advantages of the present invention will be more readily appreciated from the following detailed description taken in conjunction with the accompanying drawings, in which.

DETAILED DESCRIPTION OF THE PREFERRED EMBODIMENTS

Figure 1:
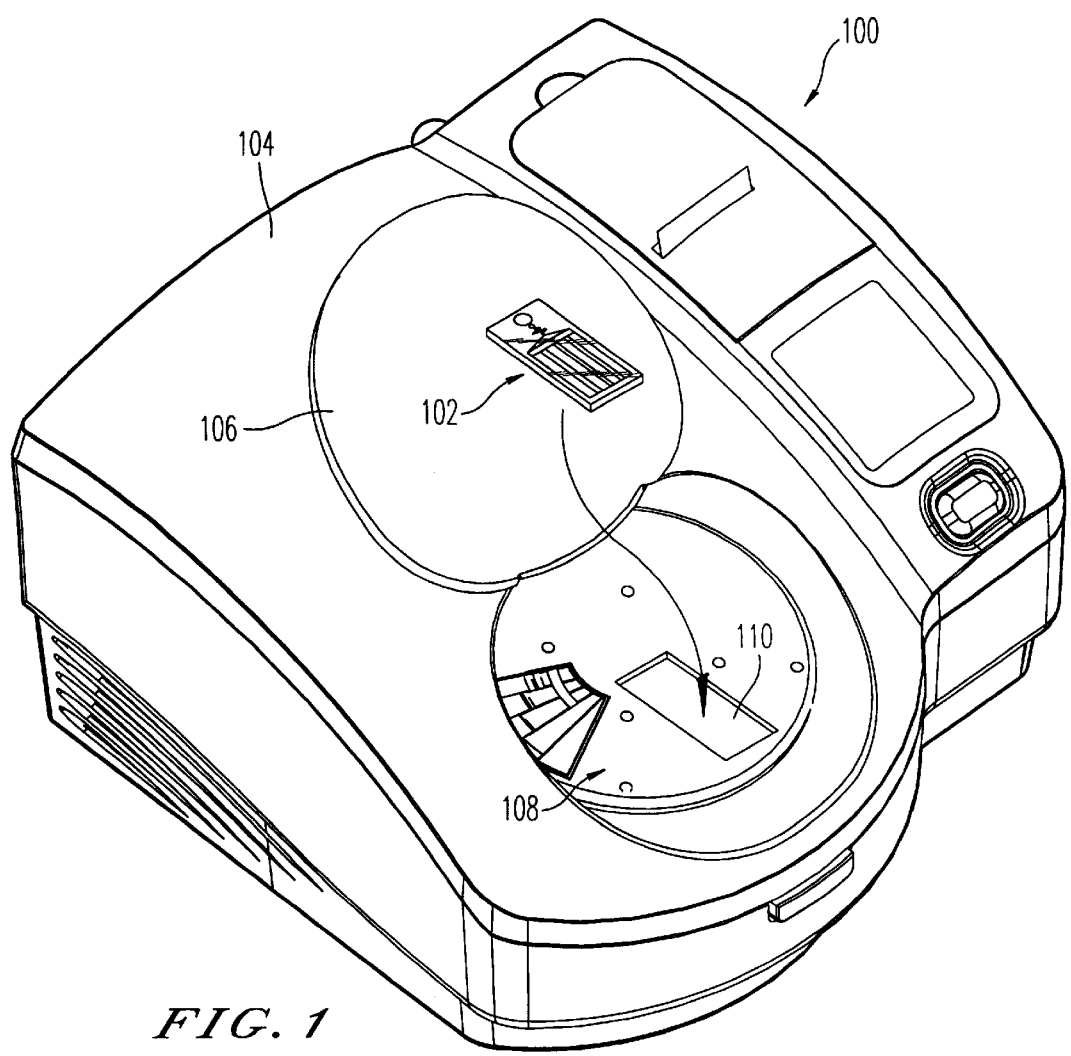
FIG. 1 is a perspective view of a centrifuge with which a fluid sample container according to the present invention is adaptable for use.

FIG. 1 illustrates an example of a centrifuge 100 with which a fluid sample container 102 according to the present invention is adaptable for use. The centrifuge 100, which can be a combined centrifuge and optical reader of the type described in the aforementioned U.S. patent applications Ser. Nos. 09/032,935, 09/032,931, 09/032,373 and 09/033,368, all of said applications being expressly incorporated by reference herein, includes a cover 104 having a door 106 for providing access to the rotor 108 which rotates to centrifuge the fluid sample. The rotor 108 includes at least one container receiving opening 110 into which can be loaded a fluid sample container 102 as shown.

When the fluid sample 102 is loaded into the container receiving opening 110 of the rotor 108, the door 106 is closed and the centrifuge 100 is controlled to rotate the rotor 108 at the desired rate to separate by density the components of the fluid sample in the fluid sample container 102. As described in more detail below, once the fluid sample has been centrifuged, the separated component layers in the centrifuged fluid sample can be read by, for example, an optical reader of the type shown schematically in FIG. 2. The optical reader 112 can be present in the centrifuge 100, as described in the four copending applications incorporated by reference above, or it may be provided in a separate reading device (not shown).

As illustrated, an optical reader 112 of this type includes a flash tube 114 which is controlled to generate a burst of light. The light is reflected by a reflector 116 through a filter 118 toward the fluid sample container 102. The light emitted from the centrifuged sample in the fluid sample container 102 passes through lens array 120, through one of the filters 122, 124 and 126 of a filter array, and is received by a CCD array 128. The CCD array 128 converts the received light into a signal representing characteristics of the components in the centrifuged fluid sample being read. The optical reader 112 can further include a light source 130, such as an LED, which emits light through the centrifuged fluid sample in the fluid sample container 102 that is received by the CCD array 128, which converts the received light into a signal representative of characteristics of the sample.

Figure 3:
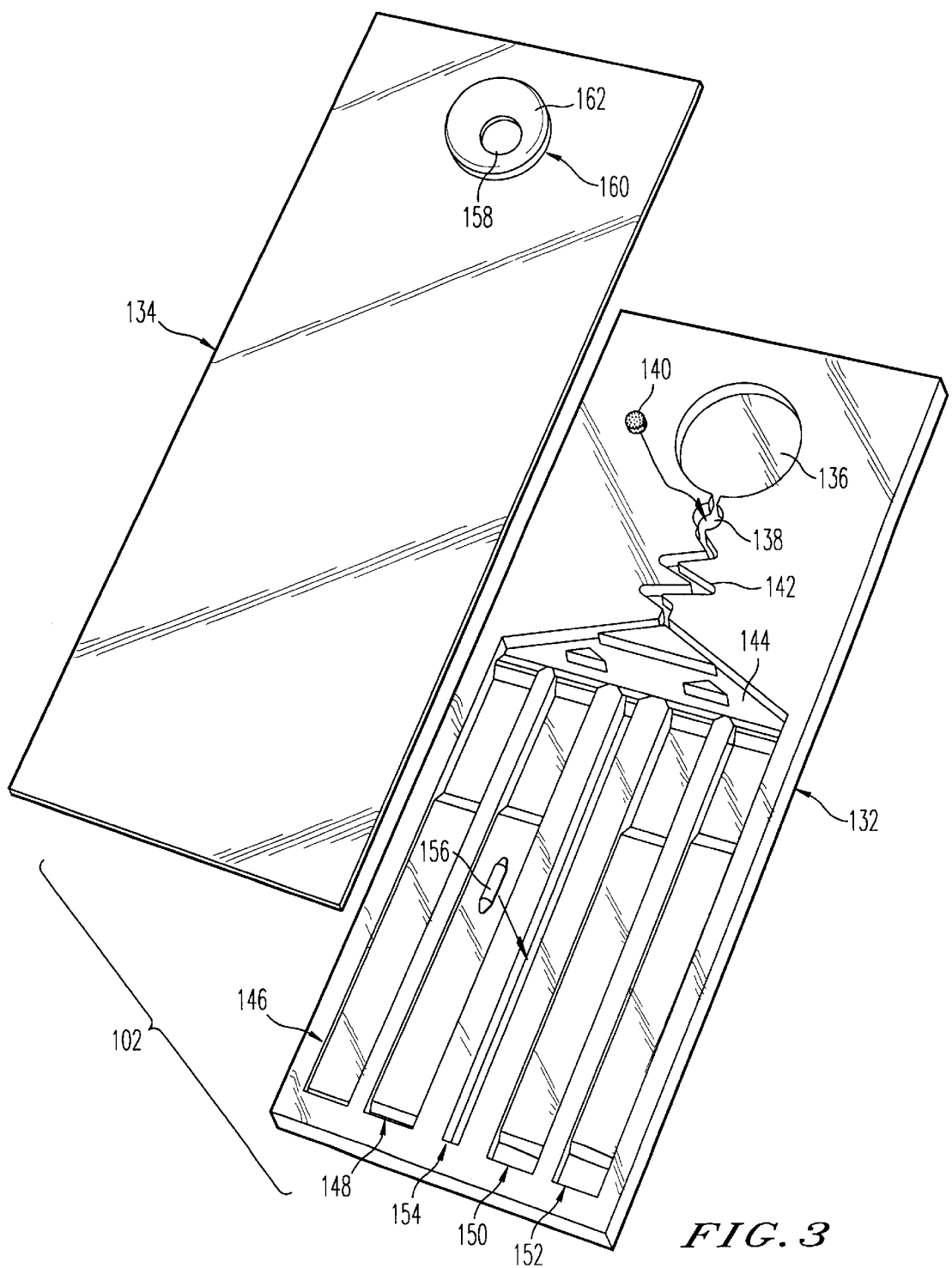
FIG. 3 is an exploded perspective view of a fluid sample container according to an embodiment of the present invention.
Figure 4:
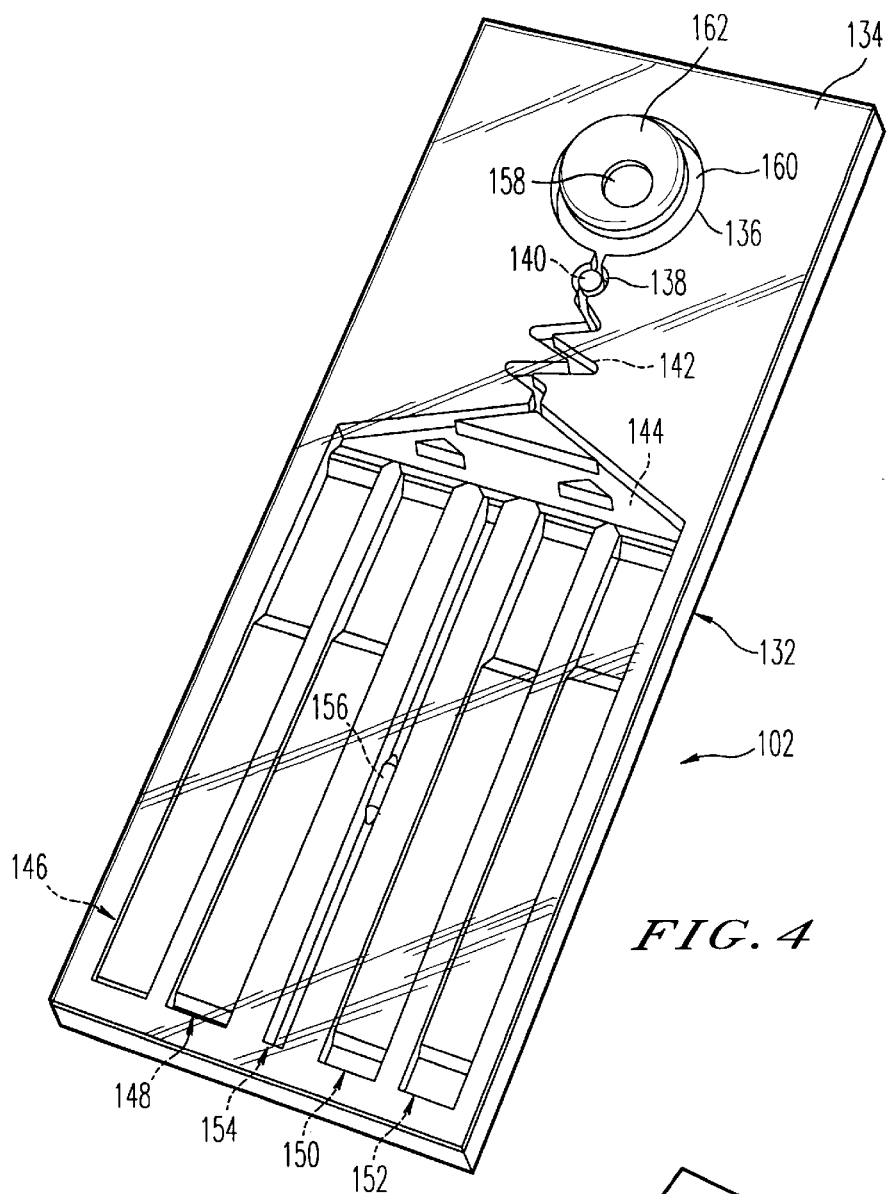
FIG. 4 is an assembled perspective view of the fluid sample container shown in FIG. 3.

An example of fluid sample container 102 according to an embodiment of the present invention is shown in more detail in FIGS. 3 and 4. As shown, fluid sample container 102 includes a base 132 and a cover 134. The base 132 and cover 134 are each preferably made of a transparent plastic material, such as transparent polystyrene or the like, and can be made by an injection molding process or any other suitable process known in the art.

Base 132 includes a fill well 136, a reagent pellet well 138 for housing a reagent pellet 140, mixing channel 142, distribution cavity 144, a plurality of expansion cavities 146, 148, 150 and 152, and a float cavity 154 having a float 156 slidably contained therein. Fill well 136 is in communication with reagent pellet well 138, which communicates with mixing channel 142. Mixing channel 142 further communicates with distribution cavity 144, which communicates with each of the expansion cavities 146–152, and with float cavity 154. Although only four expansion cavities 146–152 are shown, the container 102 can include any suitable number of expansion cavities. Also, the container 102 can include any number of fill wells and mixing channels. For example, the container 102 can include a plurality of fill wells, and a plurality of mixing channels, each providing communication between a fill well and a respective expansion cavity. Alternatively, a plurality of fill wells can communicate with one expansion cavity via a plurality of mixing channels, and so on.

Figure 5:
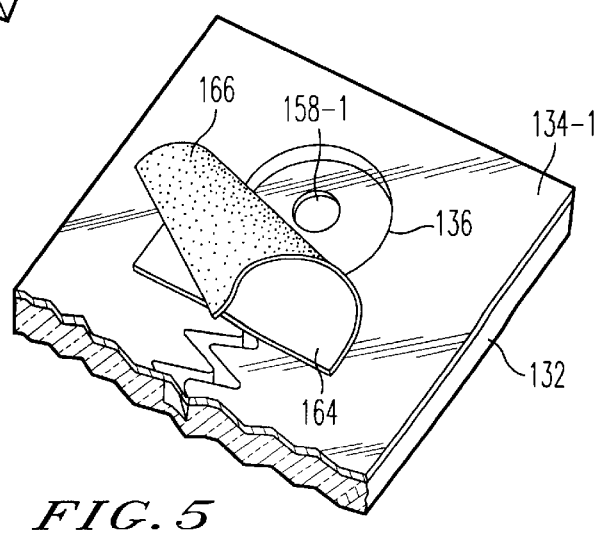
FIG. 5 is an alternative embodiment of the cover of the fluid sample container as shown in FIGS. 3 and 4.
Figure 6:
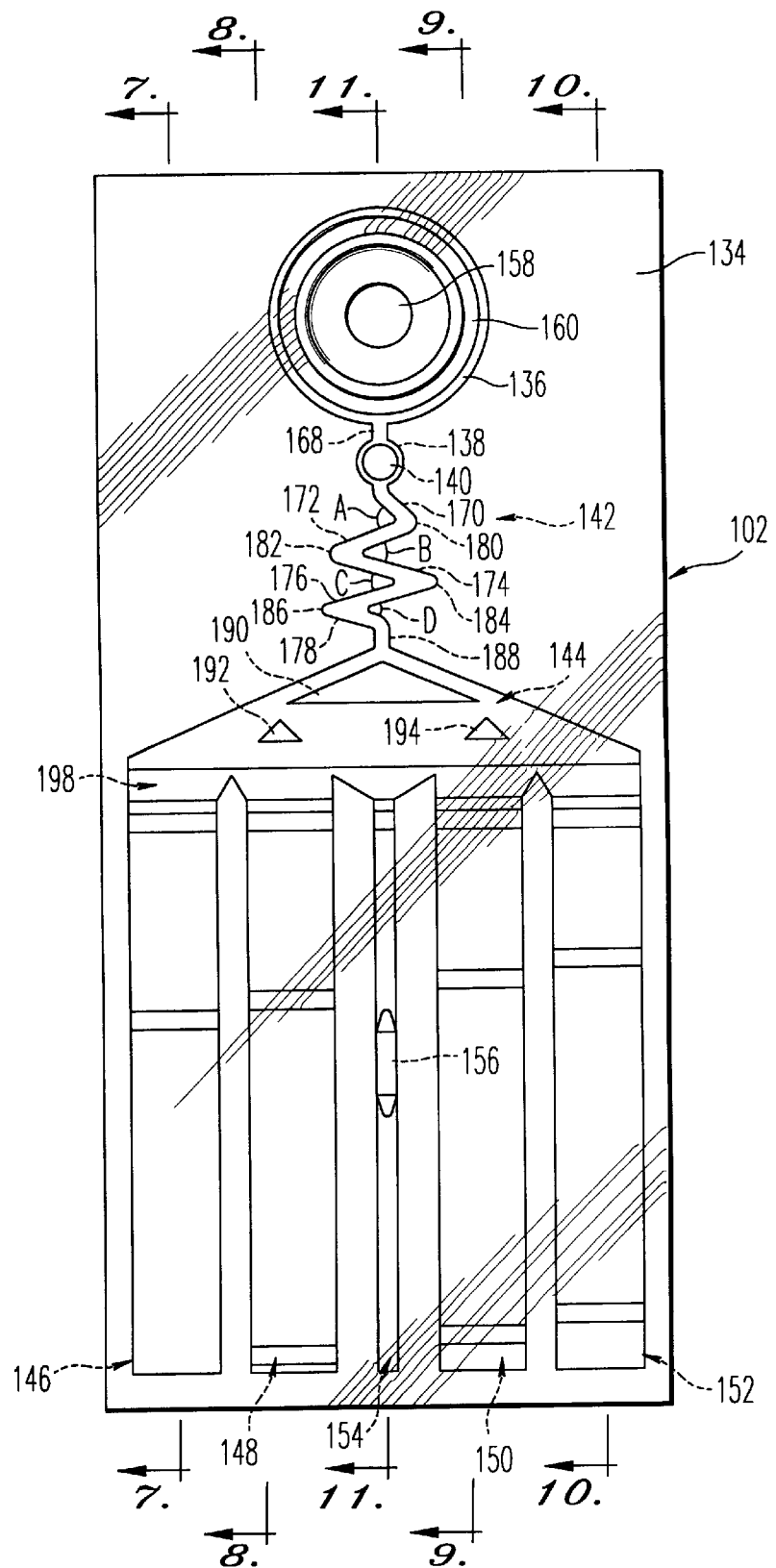
FIG. 6 is a top plan view of the fluid sample container as shown in FIGS. 3 and 4.

Cover 134 includes an opening 158 therein which communicates with fill well 136. Opening 158 can be defined by a ring-shaped raised area 160 which has a sloping inner surface 162 that directs fluid into the opening 158. Alternatively, as shown in FIG. 5, the cover can be configured as cover 134-1 which includes an opening 158-1 therein and a label 164 having an adhesive on one side thereof for removably attaching the label 164 to the cover 134-1. The cover 164 can be lifted as shown to provide access to opening 158-1 to allow the sample fluid to be deposited into the fill well 136 through the opening 158-1. The label 164 can then be placed back over opening 158-1 to provide an aerosol-tight seal over opening 158-1. Although not shown, cover 134 can include a label specifically designed to cover opening 158 in raised area 160.

Further details of the fill well 136, reagent pellet well 138, mixing channel 142, distribution cavity 144, expansion cavities 146–152, and float cavity 154 are shown in FIGS. 6–11. The fluid sample container 102 in this example has a length of 43 mm and a width of 20 mm. The base 132 has a thickness of 2.75 mm, and the cover has a thickness of about 0.76 mm (0.030 inches). The fill well 136 is circular or substantially circular in shape, and has a diameter of about 7 mm. However, the fill well 136 can have any size and shape suitable for receiving a fluid sample, such as a blood sample.

Reagent pellet well 138 is also circular or substantially circular in shape in this example, and has a diameter of about 2 mm, which is sufficient to receive a reagent pellet well 138. The reagent pellet well 138, as well as the reagent pellet 140, can have any suitable size and shape. The reagent pellet 140 includes dried dye materials, such as acridine orange, and can also include heparin and EDTA anticoagulant coatings, as well as potassium oxalate and monoclonal antibody. Reagent pellet well 138 is in communication with fill well 136 by a channel 168 which, in this example, is rectangular and has a width of about 1 mm and a height of about 1.3 mm. The channel 168, however, can have any suitable shape and cross-sectional area sufficient to allow the flow of fluid from fill well 136 to reagent pellet well 138 as described in more detail below.

Mixing channel 142 includes mixing branch 170, mixing branch 172, mixing branch 174, mixing branch 176 and mixing branch 178. All of the mixing branches have the same or substantially the same shape and cross-sectional area. In this example, each of the mixing branches has a width of about 1 mm and a height of about 1.3 mm, but the mixing branches can have any suitable cross-sectional area or shape to allow the flow of fluid therethrough. Mixing branch 170 communicates with mixing branch 172 at elbow 180, and mixing branches 170 and 172 therefore extend at an angle A with respect to each other. In this example, angle A is 30°, but can be any suitable value. As described in more detail below, mixing branches 170–178 function to redirect the fluid passing through them, to facilitate mixing of the materials contained in the reagent pellet 140 with the fluid.

As further illustrated, mixing branch 172 is coupled to mixing branch 174 by elbow 182, and mixing branches 172 and 174 extend at an angle B with respect to each other. In this example, angle B is about 30°, but can have any suitable value. Mixing branch 174 communicates with mixing branch 176 at elbow 184, and thus, mixing branch 174 extends at an angle C with respect to mixing branch 176. In this example, angle C is about 30°, but can have any suitable value. Mixing branch 176 is coupled to mixing branch 178 by elbow 186. Therefore, mixing branches 176 and 178 extend at an angle D with respect to each other, which in this example is about 30° but can have any suitable value.

The mixing channel 142 is coupled at one end to reagent pellet well 138, and is coupled at its other end to distribution cavity 144 by channel 188. Channel 188 has a cross-sectional area the same or substantially the same as the cross-sectional areas of channel 168 and mixing branches 170–178, and therefore has a width of about 1 mm and a height of about 1.3 mm. However, channel 188 can have any size and shape suitable to allow fluid to flow from the mixing channel 142 to the distribution cavity 144.

Distribution cavity 144 in this example has a triangular or substantially triangular shape as shown when viewed from the top of the fluid sample container 102. The distribution cavity 144 includes wedges 190, 192 and 194 which each have a triangular cross-section and extend upwardly from the bottom surface 196 defining the bottom of the distribution cavity 144. The wedges 190–194 function to facilitate distribution of the fluid entering the distribution cavity 144 across the entire width of the distribution cavity 144. As further illustrated, a ramped portion 198 extends in a direction toward the cover 104 at the end of the distribution cavity 144 which communicates with expansion cavities 146–152 and flow cavity 154. The ramped portion 198 has an upwardly slanted surface 200 which is pitched at an angle of about 45° with respect to a plane parallel to the bottom surface 196 of the distribution cavity 144. However, the slanted surface 200 can be slanted at any angle suitable to achieve the purpose described in more detail below. The ramped portion 198 further includes a top surface 202 that is parallel or substantially parallel to bottom surface 196 of distribution cavity 144, and also includes a downwardly slanted surface 204 that, in this example, is slanted at an angle of 45° with respect to a plane parallel to the top surface 202, but can be slanted at any angle suitable to achieve the purpose discussed below.

As described above, expansion cavities 146–152 extend parallely or substantially parallely to each other, and each expansion cavity communicates with distribution cavity 144. Also, expansion cavities 146–152 have the same or substantially the same volume.

Figure 7:
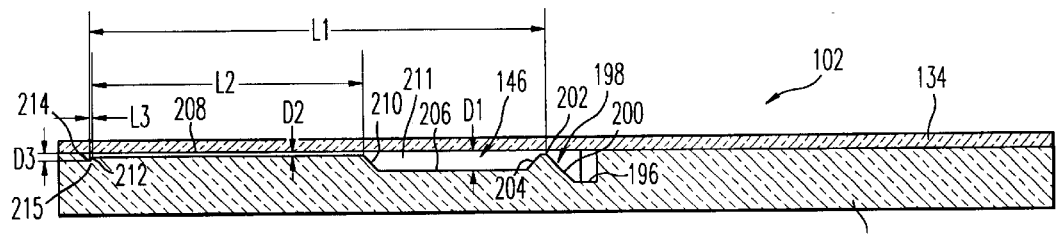
FIG. 7 is a cross-sectional view of the fluid sample container taken along line 7—7 in FIG. 6.

As shown in FIG. 7, expansion cavity 146 is 20 mm long as measured between the point of intersection of upwardly slanted surface 200 and top surface 202 of ramped portion 198, and the opposite end of expansion cavity 146 as shown by line L1. However, expansion cavity 146 can have any suitable length. Expansion cavity 146 includes a lower surface 206 which is parallel or substantially parallel to the inner surface of cover 134 at a distance of 1.0 mm from the inside surface of cover 134. Expansion cavity 146 further includes an upper surface 208 and a slanted surface 210 connecting lower surface 206 to upper surface 208. The region of expansion cavity 146 defined between the inner surface of cover 134 and slanted surface 210 and lower surface 206 is a first collection region 211, the purpose of which is described in more detail below.

In this example, upper surface 208 has a length L2 of 12 mm (or any other suitable value), and slanted surface 210 extends at an angle of 60°, or about 60°, with respect to a plane parallel to lower surface 206. However, this angle can be any practical value suitable to achieve the function described below. Furthermore, in this example, upper surface 208 is at a distance L3 of 0.099 mm from the end of the expansion cavity 146, and the distance D2 from the upper surface 208 to the inner surface of cover 134 is 0.1 mm, which is one-tenth the distance from lower surface 206 to the inner surface of cover 134. The purpose of this arrangement is described in more detail below. The ratio of the distances D2 to D1 can be any value suitable to achieve the purpose described below.

As further illustrated, expansion cavity 146 includes a second slanted surface 212 and a second lower surface 214. The second slanted surface 212 connects second lower surface 214 to upper surface 208. The distance D3 from second lower surface 214 to the inner surface of cover 134 is nominal. Second slanted surface 212 extends at an angle at of about 60° with respect to a plane parallel to lower surface 206. However, this angle can be any angle suitable to achieve the purpose described below. The region of expansion cavity 146 defined between the inner surface of cover 134 and second slanted surface 212 and second lower surface 214 is a second collection region 215, the purpose of which is described in more detail below.

Figure 8:
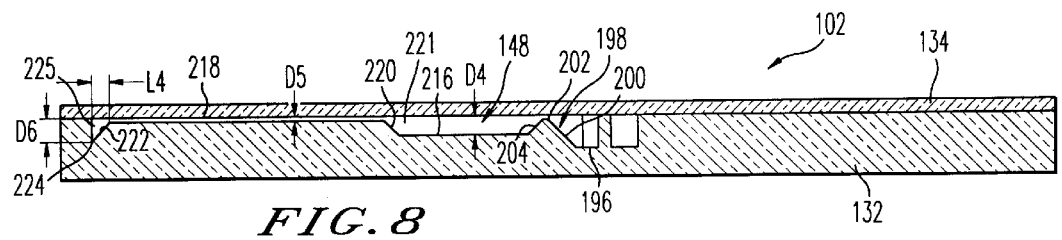
FIG. 8 is a cross-sectional view of the fluid sample container taken along line 8—8 in FIG. 6.

As shown in FIG. 8, expansion cavity 148 has the same or substantially the same overall length L1 (20 mm) as expansion cavity 146, and includes a lower surface 216 which is parallel or substantially parallel to the inner surface of cover 134 at a distance D4 of 1.0 mm from the inner surface of cover 134. Expansion cavity 148 further includes an upper surface 218 and a slanted surface 220 connecting lower surface 216 to upper surface 218. The region of expansion cavity 148 defined between the inner surface of cover 134 and slanted surface 220 and lower surface 216 is a first collection region 221, the purpose of which is described in more detail below.

In this example, slanted surface 220 extends at an angle of 60°, or about 60°, with respect to a plane parallel to lower surface 216. However, this angle can be any practical values suitable to achieve the function described below. Furthermore, in this example, upper surface 218 has the same or substantially the same length L2 (12 mm) as upper surface 208 of expansion cavity 156. The distance D5 from the upper surface 218 to the inner surface of cover 134 is 0.1 mm, which is one-tenth the distance from lower surface 216 to the inner surface of cover 134. Upper surface 218 is at a distance L4 of 0.759 mm from the end of the expansion cavity as shown. The purpose of this arrangement is described in more detail below. The ratio of the distances D5 to D4 can be any value suitable to achieve the purpose described below.

As further illustrated, the expansion cavity 148 includes a second slanted surface 222, and a second lower surface 224 which is parallel to a plane parallel to lower surface 216. The second slanted surface 222 connects second lower surface 224 to upper surface 218. The distance D6 from second lower surface 224 to the inner surface of cover 134 is equal to, or about equal to, distance D4, which is 1.0 mm. Second slanted surface 222 extends at an angle of about 60° with respect to a plane parallel to second lower surface 224. However, this angle can be any angle suitable to achieve the purpose described below. The region of expansion cavity 148 defined between the inner surface of cover 134 and second slanted surface 222 and second lower surface 224 is a second collection region 225, the purpose of which is described in more detail below.

Figure 9:
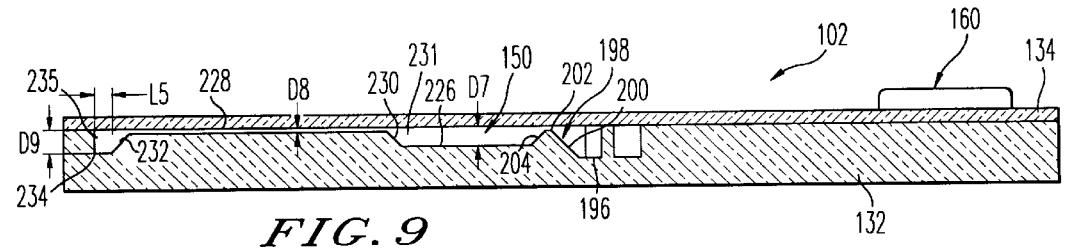
FIG. 9 is a cross-sectional view of the fluid sample container taken along line 9—9 in FIG. 6.

As shown in FIG. 9, expansion cavity 150 has the same or substantially the same overall length L1 as expansion cavity 146, and includes a lower surface 226 which is parallel or substantially parallel to the inner surface of cover 134 at a distance D7 of 1.0 mm from the inner surface of cover 134. Expansion cavity 150 further includes an upper surface 228 having the same or substantially the same length L2 as upper surface 208 of expansion cavity 146, and a slanted surface 230 connecting lower surface 226 to upper surface 228. The region of expansion cavity 150 defined between the inner surface of cover 134 and slanted surface 230 and lower surface 226 is a first collection region 231, the purpose of which is described in more detail below.

In this example, slanted surface 230 extends at an angle of 60°, or about 60°, with respect to a plane parallel to lower surface 226. However, this angle can be any practical value suitable to achieve the function described below. Furthermore, in this example, the distance D8 of 0.1 mm from the upper surface 228 to the inner surface of cover 134 is one-tenth the distance from lower surface 226 to the inner surface of cover 134. Upper surface 228 is at a distance L5 of 1.456 mm from the end of the expansion cavity as shown. The purpose of this arrangement is described in more detail below. The ratio of the distances D8 to D7 can be any value suitable to achieve the purpose described below.

As further illustrated, the expansion cavity 150 includes a second slanted surface 232 and a second lower surface 234 which is parallel to a plane parallel to lower surface 226. The second slanted surface 232 connects second lower surface 234 to upper surface 228. The distance D9 from second lower surface 234 to the inner surface of cover 134 is equal to, or about equal to, distance D7, which is 1.0 mm. Second slanted surface 232 extends at an angle of about 60° with respect to a plane parallel to second lower surface 234. However, this angle can be any angle suitable to achieve the purpose described below. The region of expansion cavity 150 defined between the inner surface of cover 134 and second slanted surface 232 and second lower surface 234 is a second collection region 235, the purpose of which is described in more detail below.

Figure 10:
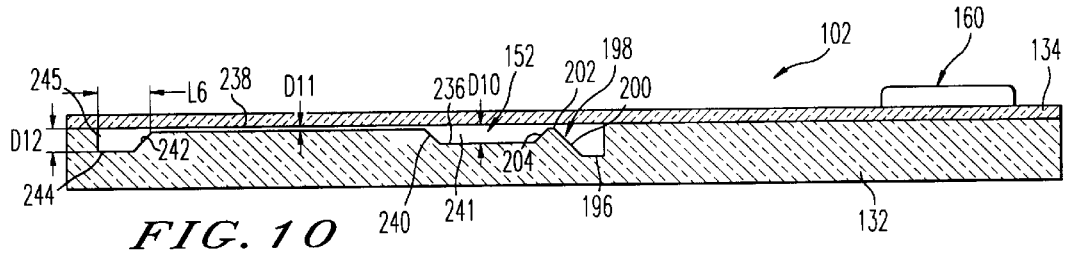
FIG. 10 is a cross-sectional view of the fluid sample container taken along line 10—10 in FIG. 6.
Figure 11:
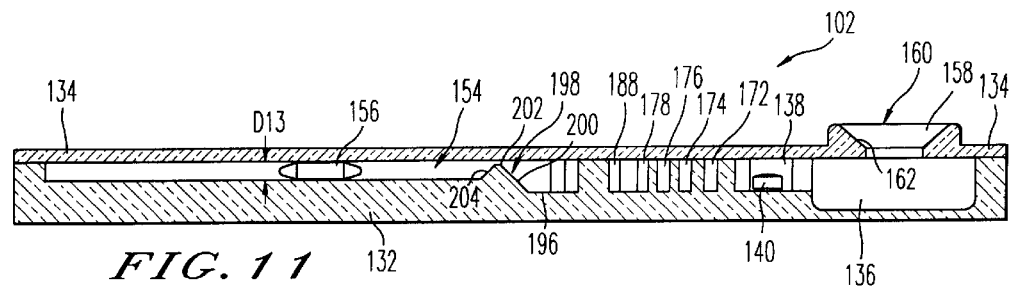
FIG. 11 is a cross-sectional view of the fluid sample container taken along line 11—11 in FIG. 6.
Figure 12:
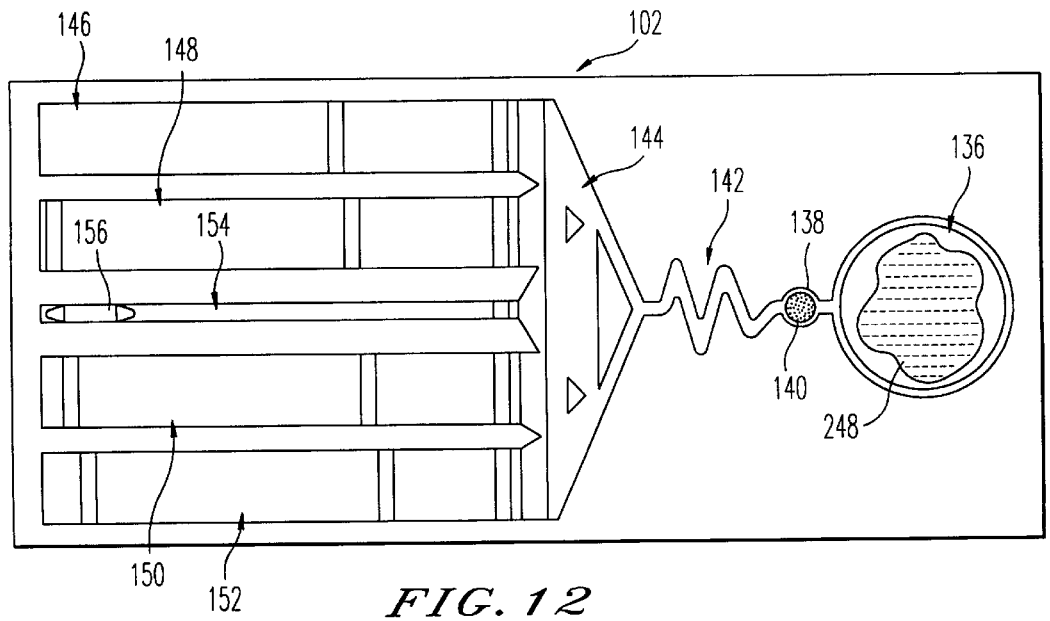
FIG. 12 is a schematic diagram illustrating the loading of a blood sample into the fill well of the fluid sample container shown in FIGS. 3 and 4.

As shown in FIG. 10, expansion cavity 152 has the same or substantially the same overall length L1 as expansion cavity 146, and includes a lower surface 236 which is parallel or substantially parallel to the inner surface of cover 134 at a distance D10 of about 1.0 mm from cover 134. Expansion cavity 152 further includes an upper surface 238 having the same or substantially the same length L2 as upper surface 208 of expansion cavity 146, and a slanted surface 240 connecting lower surface 236 to upper surface 238. The region of expansion cavity 152 defined between the inner surface of cover 134 and slanted surface 240 and lower surface 236 is a first collection region 241, the purpose of which is described in more detail below.

In this example, slanted surface 240 extends at an angle of 60°, or about 60°, with respect to a plane parallel to lower surface 236. However, this angle can have any practical value suitable to achieve the function described below. Furthermore, in this example, the distance D11 of 0.1 mm from the upper surface 238 to the inner surface of cover 134 is one-tenth the distance from lower surface 236 to the inner surface of cover 134. Upper surface 238 is at a distance L6 of 2.153 mm from the end of the expansion cavity as shown. The purpose of this arrangement is described in more detail below. The ratio of the distances D11 to D10 can be any value suitable to achieve the purpose described below.

As further illustrated, the expansion cavity 150 includes a second slanted surface 242 and a second lower surface 244 which is parallel to a plane parallel to lower surface 236. The second slanted surface 242 connects second lower surface 244 to upper surface 238. The distance D12 from second lower surface 244 to the inner surface of cover 134 is equal to, or about equal to, distance D10, which is 1.0 mm. Second slanted surface 242 extends at an angle of about 60° with respect to second lower surface 244. However, this angle can have any value suitable to achieve the purpose described below. The region of expansion cavity 152 defined between the inner surface of cover 134 and second slanted surface 242 and second lower surface 244 is a second collection region 245, the purpose of which is described in more detail below.

As further illustrated, float cavity 156 is positioned between expansion cavities 148 and 150, and extends parallel or substantially in parallel to expansion cavities 146–152. Float cavity 156 includes a bottom surface 246 which is at a distance D13 of 0.9 mm from the inner surface of cover 134. The float cavity 156 has a width of about 0.9 mm in this example, and thus has a cross-sectional area sufficient to accommodate float 156. As described in more detail below, the outer diameter of float 156 is slightly smaller than the width of float cavity 154, to enable float 156 to move along float cavity 154 when fluid enters the float cavity 154.

The operation of the fluid sample container 102 will now be described with regard to FIGS. 12–18. In this description, the fluid sample being placed in the fluid sample container 102 is a blood sample that is to be centrifuged so that a complete blood count can be taken. However, the fluid sample container 102 can be used with any fluid, especially those having components with different densities that cause the components to arrange themselves in density layers when the fluid sample is centrifuged.

As described above, a blood sample can be collected by the venus method or by the capillary method. In either event, the sample is introduced into fill well 136 through opening 158 in the cover 134. As discussed above, the cover 134 can include a label which covers the opening 158, or can be configured as cover 134-1.

Figure 13:
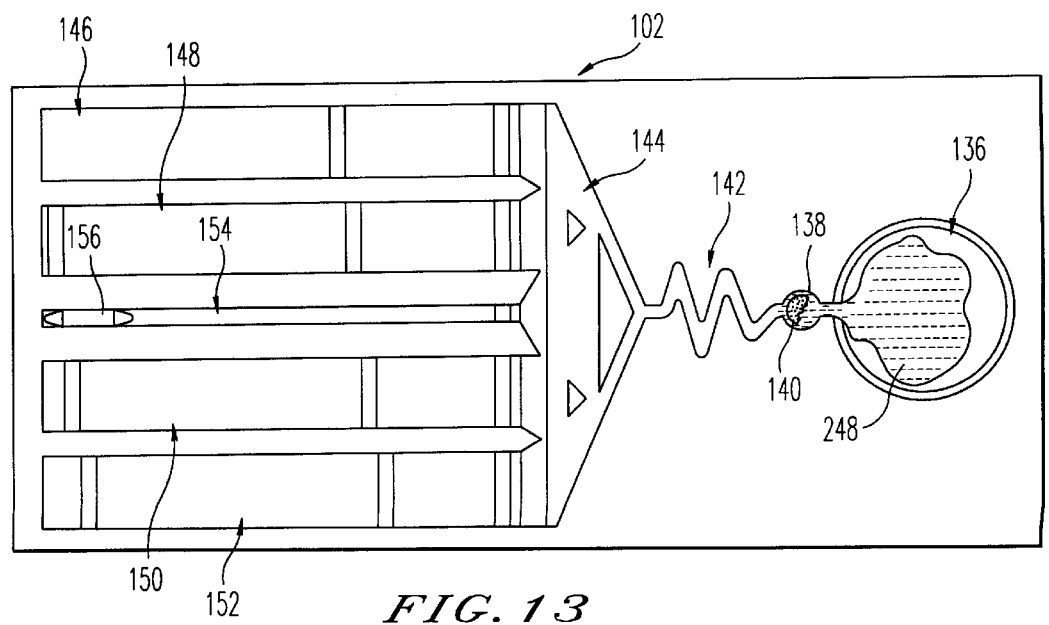
FIG. 13 is a schematic diagram showing the blood sample contained in the fill well beginning to flow into the mixing channels of the fluid sample container shown in FIGS. 3 and 4.

Once the blood has been placed into fill well 136, the fluid sample container 102 can be placed in the container-receiving opening 110 in rotor 108 as shown in FIG. 1, with the fill well 136 radially inward toward the rotational axis of rotor 108. The centrifuge 100 is then controlled to begin spinning rotor 108 at a desired mixing speed, which can be in the range of 1,000–2,000 rpm. As the rotor 108, and hence the fluid sample in container 102, begin to spin, the centrifugal force acting on the blood 248 in fill well 136 begins to move the blood through channel 168 where it contacts reagent pellet 140 in reagent pellet well 138 as shown in FIG. 13. The blood 248 then begins to dissolve reagent pellet 140. Also, the centrifugal force acting on the float 156 moves the float 156 to the end of float cavity 154 as shown.

Figure 14:
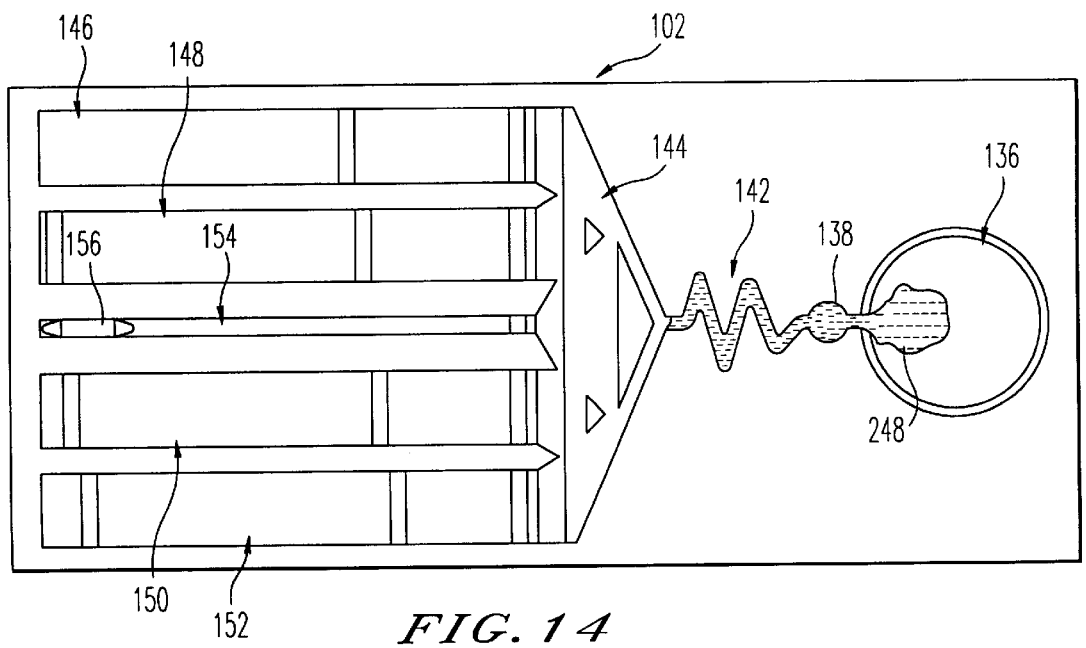
FIG. 14 is a schematic diagram showing the blood sample flowing into the distribution cavity of the fluid sample container shown in FIGS. 3 and 4.
Figure 15:
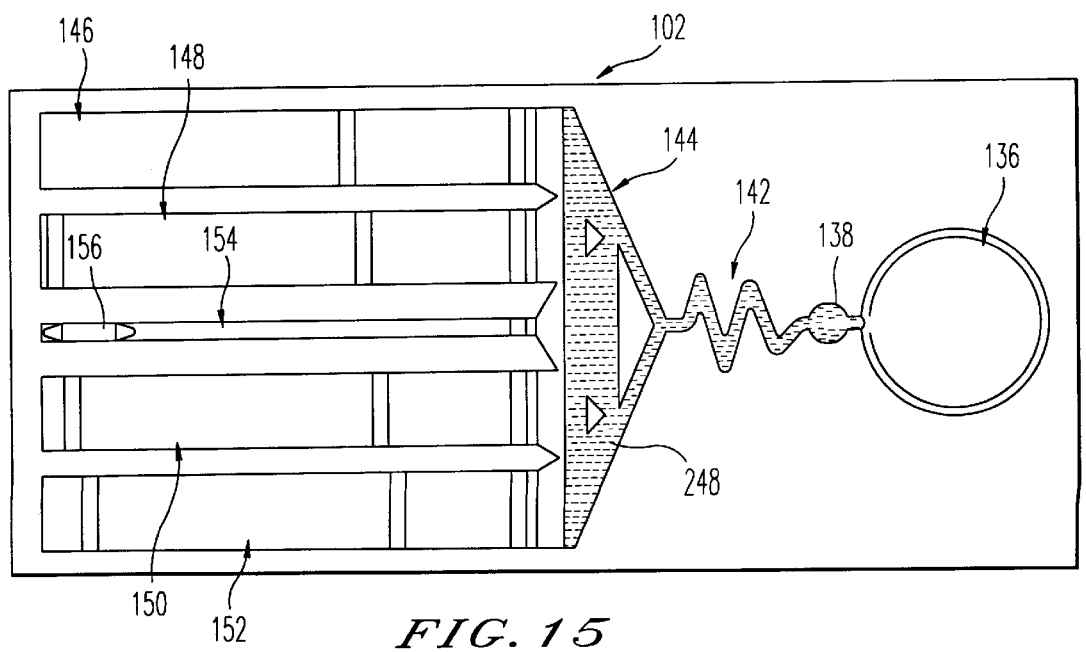
FIG. 15 is a schematic diagram showing the blood sample in the distribution cavity of the fluid sample container shown in FIGS. 3 and 4.
Figure 16:
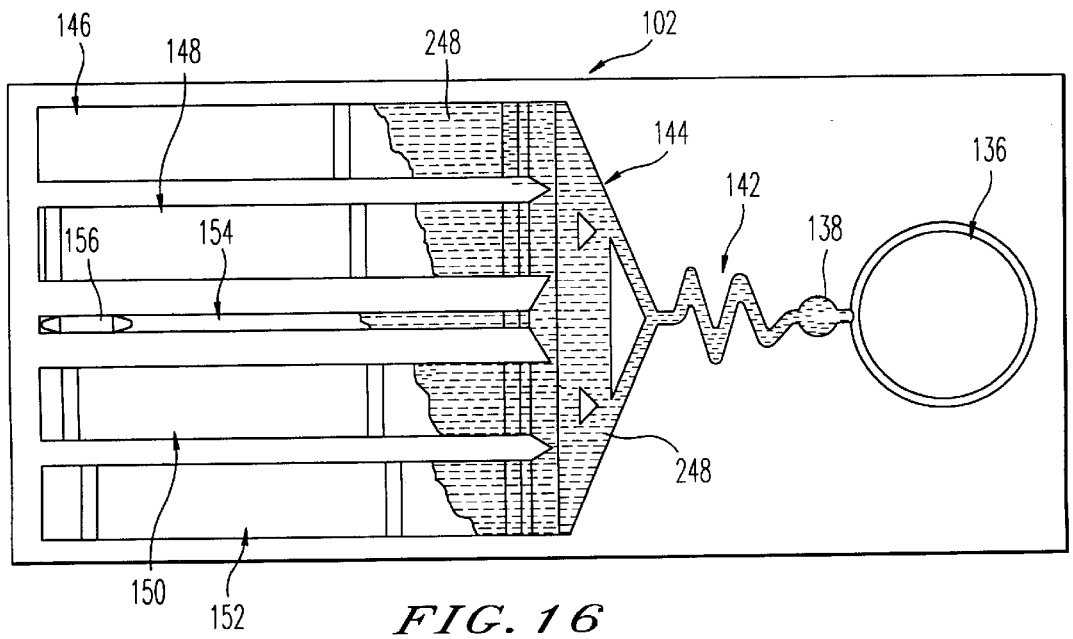
FIG. 16 is a schematic diagram showing the blood sample spilling over the ramp separating the distribution cavity from the expansion cavities of the fluid sample container shown in FIGS. 3 and 4.
Figure 17:
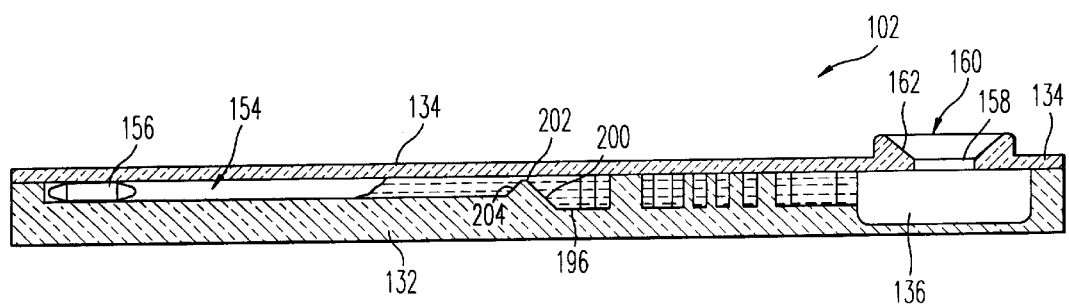
FIG. 17 is a cross-sectional view of the fluid sample container showing the blood sample spilling over the ramp as shown in FIG. 16.
Figure 18:
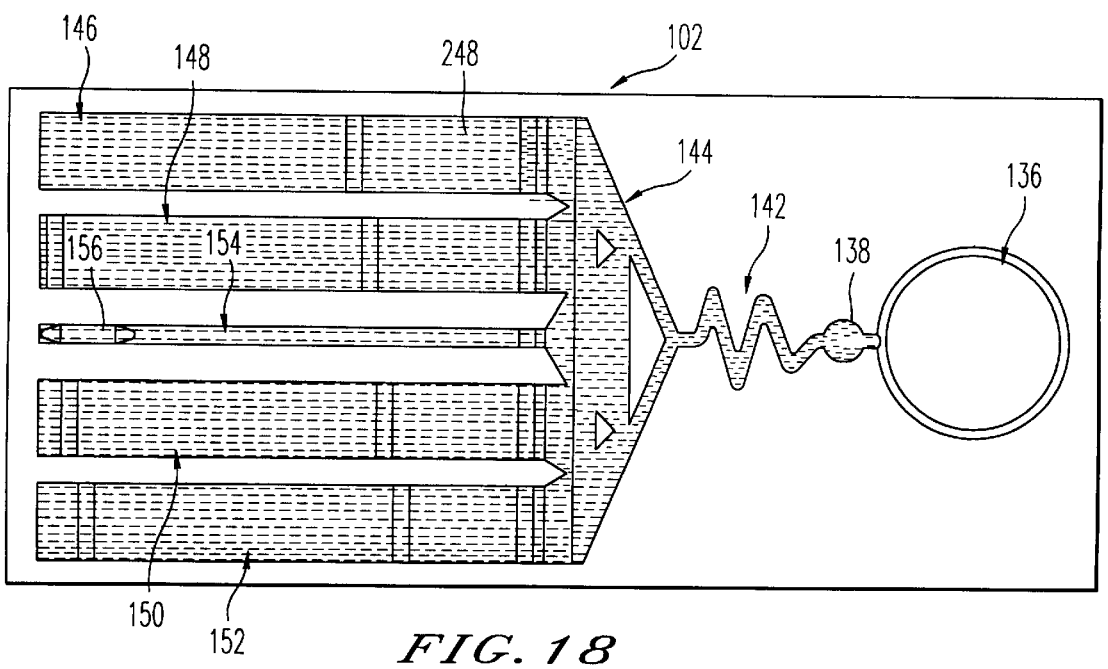
FIG. 18 is a schematic diagram showing blood filling the expansion cavities of the fluid sample container shown in FIGS. 3 and 4.

While dissolving reagent pellet 140, the blood 248 continues to flow through reagent pellet well 138 and into mixing channel 142 as shown in FIG. 14. As the blood 248 flows through the mixing channel 142, the zig-zag pattern of the mixing channel 142 causes the reagents and dyes present in the reagent pellet 140 to mix with the blood 248. As shown in FIG. 15, the blood continues to flow through mixing channel 142 and empties into distribution cavity 144, where it is distributed through the aid of wedges 190–194 through the entire width of distribution cavity 144. However, as shown in FIG. 15, the ramped portion 198 prevents the blood 248 from continuing to flow into the expansion cavities 146–152 and float cavity 154. The centrifuge 100 then begins to rotate the rotor 108 at the centrifuging speed, which can be within the range of 10,000–12,000 rpm. The additional centrifugal force imposed on blood 248 by this higher rotational speed is sufficient to cause blood 248 to flow up the upwardly slanted surface 200, over the top surface 202 and down the downwardly slanted surface 204 into the expansion cavities 146–152 and float cavity 154. This centrifugal force is also sufficient to force the blood 248 to flow up the slanted surfaces 210, 220, 230 and 240 of expansion cavities 146, 148, 150 and 152, respectively, and onto the respective upper surfaces 208, 218, 228 and 238. The blood then flows down the second slanted surfaces 212, 222, 232 and 242, and into the respective second lower surfaces 214, 224, 234 and 244 of the expansion cavities 146, 148, 150 and 152, respectively. At this time, blood is also flowing into float cavity 154. Accordingly, as shown in FIG. 18, the blood fills expansion cavities 146–152, and float cavity 154. The space between the outer diameter of the float 156 and the float cavity 154 is sufficient to allow blood to pass around the float 156 and hence, the float 154 becomes suspended in the blood.

Figure 19:
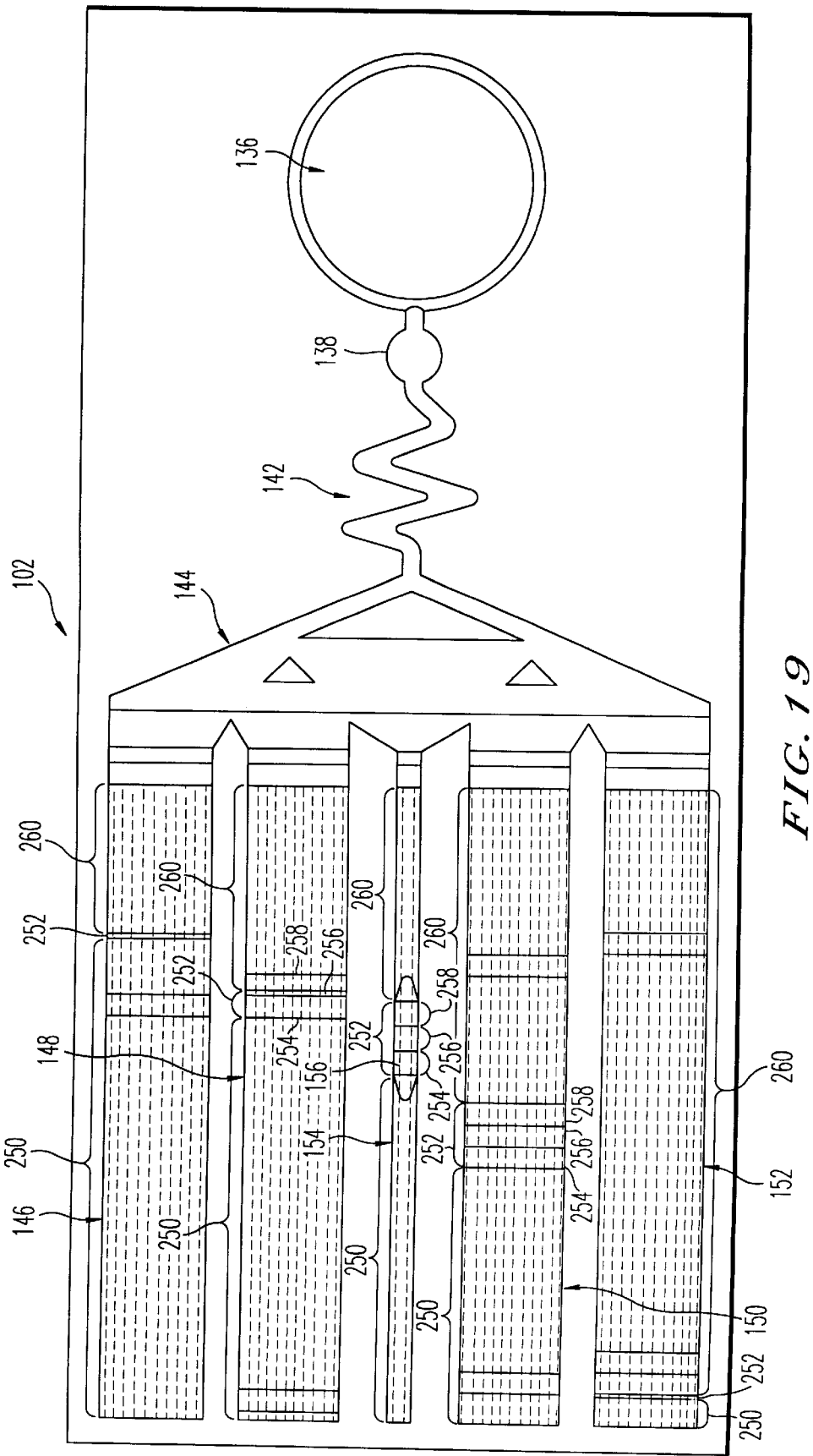
FIG. 19 is a schematic diagram showing the components of the blood sample separated into their respective density layers due to the centrifuging.

As the centrifugation continues, the blood components begin to separate into their respective density layers in a manner similar to that which occurs in known glass blood tubes. As shown in FIG. 19, the component layers comprise a red blood cell layer 250, and a buffy coat layer 252 comprising a granulocyte layer 254, a mixed lymphocyte and monocyte layer 256, and a platelet layer 258. The centrifuged blood sample further includes a plasma layer 260.

As can be appreciated from FIG. 19 in particular, the upper surfaces 208, 218, 228 and 238 of the expansion cavities 146–152, respectively, are positioned to expand certain component layers and, in particular, the buffy coat layer 252. The different distances of the edges of the upper surfaces 208, 218, 228 and 238 from the ends of their respective expansion cavities 146–152 of the fluid sample container 102 are intended to compensate for variation in the number of, for example, the red blood cells in the blood sample which affects the location in the expansion cavities 146–152 at which the buffy coat layer 252 appears.

That is, since the volumes of each of the expansion cavities 146–152 are equal or essentially equal, equal or essentially equal volumes of blood sample will collect in each of the expansion cavities 146–152. Hence, each expansion cavity 146–152 will contain an amount of red blood cells, granulocytes, lymphocytes, monocytes, platelets and plasma equal to that of any other expansion cavity 146–152.

Due to the centrifugation, the red blood cells in the blood sample become compacted toward the ends of the expansion cavities 146–152 opposite to the ends of the expansion cavities 146–152 at which the ramped portion 198 is present. As shown in FIG. 7, the second collection region 215, which is defined between the inner surface of cover 134 and the second slanted surface 212 and the second lower surface 214, occupies only a small portion of expansion cavity 146. Accordingly, only a small number of red blood cells will collect in the second collection region 215 of expansion cavity 146. Therefore, depending on the number of red blood cells in the sample, a portion of the red blood cells will occupy the region of the expansion cavity 146 between the inner surface of cover 134 and upper surface 208, and if the number of red blood cells in the sample is high enough, the remainder of the red blood cells occupies a portion of the first collection region 211 of expansion cavity 146 that exists between the inner surface of cover 134 and the first slanted surface 220 and lower surface 216. In this event, the reduced cross-sectional area of expansion cavity 146 defined by upper surface 208 and the inner surface of cover 134 does not expand the buffy coat layer 252, which appears in the first collection region 211 of the expansion cavity 146. Rather, that reduced cross-sectional area of expansion cavity 146 expands a portion of the red blood cell layer.

As shown in FIG. 8, the second collection region 225 of expansion cavity 148 defined between the inner surface of cover 134 and second slanted surface 222 and second lower surface 224 has a larger volume than that of the corresponding second collection region 215 of expansion cavity 46 described above. Accordingly, a larger number of red blood cells collect in second collection region 225 of expansion cavity 148. Since the amount of red blood cells in expansion cavity 148 is equal to or essentially equal to the amount of red blood cells in expansion cavity 146, the red blood cells will also be present between the inner surface of cover 134 and upper surface 218.

However, since more of the red blood cells have collected in second collection region 225 of expansion cavity 148, not enough red blood cells remain to enter first collection region 221 of expansion cavity 148. Hence, in this example, the buffy coat layer 252 appears at the end of the upper surface 218 adjacent first slanted surface 220. Accordingly, as shown in FIG. 19, a portion (e.g., granulocyte layer 254) of the buffy coat layer 252 is expanded by the reduced cross-section of expansion cavity 148 between upper surface 218 and the inner surface of cover 134, while the remainder of buffy coat layer 252 exists in the first collection region 221 adjacent upper surface 218. Thus, the buffy coat layer 252 is not properly expanded for reading.

As shown in FIG. 9, the second collection region 235 of expansion cavity 150 has a larger volume than that of second collection region 225 of expansion cavity 148 described above. Hence, a larger number of red blood cells collect in the second collection region 235 of expansion cavity 150 than in second collection region 225 of expansion cavity 148.

Since the amount of red blood cells in expansion cavity 150 is equal to the amount of red blood cells in expansion cavity 148, the red blood cells in expansion cavity 150 will occupy only a portion of the region of expansion cavity 150 between upper surface 228 and the inner surface of cover 134.

Accordingly, as shown in FIG. 19, the buffy coat layer 252 will be positioned between upper surface 228 and the inner surface of cover 134, and thus, the length of buffy coat layer 252 is expanded (i.e., by a factor of 10) due to the reduced cross-sectional area of expansion cavity 150 between upper surface 228 and the inner surface of cover 134.

Therefore, the individual layers 254, 256 and 258 of buffy coat layer 252 are more readily ascertainable in expansion cavity 150.

As shown in FIG. 10, the second collection region 245 of expansion cavity 152 has a larger volume than that of second collection region 235 of expansion cavity 150. Hence, a larger number of red blood cells collect in the second collection region 245 of expansion cavity 152 than in second collection region 235 of expansion cavity 150. Since the amount of red blood cells in expansion cavity 152 is equal to the amount of red blood cells in expansion cavity 150, the red blood cells in expansion cavity 152 will all collect in this larger second collection region 245. Accordingly, the buffy coat layer 252, and some of the plasma layer 260, will collect in second collection region 245. Therefore, buffy coat layer 252 is not expanded by the reduced cross-sectional area of expansion cavity 152 between upper surface 238 and the inner surface of cover 134.

Accordingly, in a sample having the number of red blood cells in the example described above, the buffy coat layer 252 appears expanded on upper surface 228 of expansion cavity 150. However, in a blood sample having a slightly lower number of red blood cells, the buffy coat layer may appear expanded on upper surface 218 of expansion cavity 148. That is, the volume of the second collection region 225 of expansion cavity 148 could be sufficient to collect the appropriate amount of this lesser number of red blood cells to result in the buffy coat layer 252 being positioned on the upper surface 218 of expansion cavity 148, and thus expanded by the reduced cross-sectional area of the expansion cavity 148 between upper surface 218 and the inner surface of cover 134. On the other hand, the larger volume of second collection region 235 of expansion cavity 150 would collect all of this lesser number of red blood cells, resulting in the buffy coat layer 252 being positioned unexpanded in the second collection region 225.

In a blood sample having even a lower number of red blood cells, the buffy coat layer 252 may appear expanded on upper surface 208 of expansion cavity 146, because the smaller volume of the second collection region 215 of expansion cavity 146 could be sufficient to collect the appropriate amount of this lesser number of red blood cells to suitably position buffy coat layer 252 on upper surface 208. Alternatively, in a blood sample having a larger number of red blood cells, the buffy coat layer may appear expanded on upper surface 238 of expansion cavity 152.

The fluid sample container 102 is designed such that the upper surfaces 208, 218, 228 and 238 are at different distances from the ends of their respective expansion cavities 146–152 as shown to accommodate for normal variations in the amount of red blood cells that would be found in normal human blood samples taken from different people, and to thus insure that the buffy coat region 252 will appear expanded on at least one of the upper surfaces 208, 218, 228 and 238. Although in this example, the lengths of upper surfaces 208, 218, 228 and 238 are the same or essentially the same, the lengths of these upper surfaces, and their positions with regard to the ends of their respective expansion cavities could be varied, as long as the purpose described above is achieved (i.e., it is likely that the buffy coat layer 252 will be expanded by at least one expansion cavity having a known volume).

As further illustrated, the component layers of the centrifuged sample also appear in float cavity 154 due to the centrifugation. The float 156 travels in a direction away from the end of the float cavity 154 as the red blood cells become packed at that end. Due to the density of the float 156, the float 156 becomes suspended in the centrifuged blood sample at a location at which the buffy coat layer 252 appears in the float cavity 154. Hence, the float 156 expands the length of the buffy coat layer 252 by a factor of, for example, 5 to 7 in a manner similar to a conventional float as described in the background section above.

Once the centrifugation process has been completed, the fluid sample container 102 can be removed from the centrifuge 100 and placed in an optical reader device (not shown). Alternatively, if the centrifuge 100 includes an optical reader 112 (as shown in FIGS. 1 and 2), the readings can be taken with the fluid sample container 102 remaining on the rotor 108.

Figure 2:
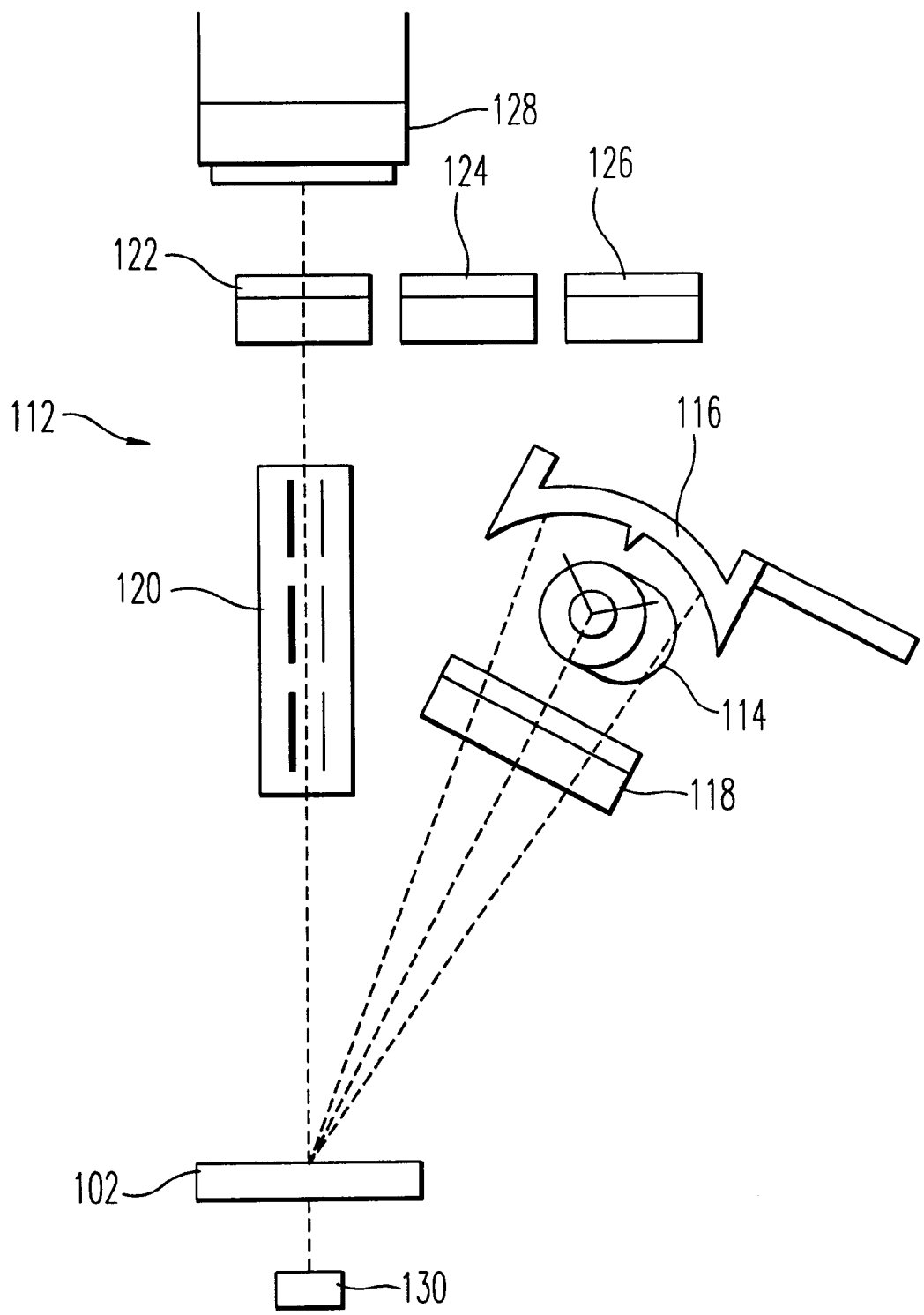
FIG. 2 is a schematic view of an optical reader adaptable for reading layers in the centrifuged fluid sample in the container.

In either event, the fluid sample container 102 is positioned with respect to the optical reader 112 as shown in FIG. 2 when readings are to be taken. That is, the fluid sample container 102 is positioned so that its length extends along the direction in which the charge-coupled devices extend in the CCD array 128. The light source 130 is energized to generate light which passes through fluid sample container 102 and is detected by CCD array 128. This "pass through" light is used to detect the location of the float 156 in float cavity 154. The detected location of the float 156, as well as the distance in which the float extends into the red blood cell layer 250, is used to calculate the density of the red blood cells (RBCs) which is proportional to hemoglobin concentration. The transmission location of the top of the RBC layers in the other cavities could be used to position the CCD array 128 at the appropriate position along the length of the expansion cavities 146–152 to read the buffy coat region 252. However, a CCD array 128 can have a length (e.g., about 27 mm) longer than the lengths of each of the expansion cavities 146–152 in this example. In this event, the CCD array 128 need only be positioned generally centrally along the length of the expansion cavity to be read, so that the CCD array 128 can receive light from the entire centrifuged sample in that particular expansion cavity.

When reading of the centrifuged sample is to be performed while the container 102 remains in centrifuge 100, the optical reader 112 is controlled to take a buffy coat reading when the rotating rotor 108 is oriented such that one of the expansion cavities (e.g., expansion cavity 146) is positioned below CCD array 128, and the CCD array is 128 at the appropriate position along the length of the expansion cavity to be read. That is, the CCD array 128 is moved in a direction radially of the rotor 108 so that the CCD array 128 is at the appropriate radial distance from the axis of rotation of the rotor 108 to receive light from the sample in the expansion cavity to be read (e.g., expansion cavity 146). The flash tube 114 is activated to radiate light onto the fluid sample container 102.

The light causes the dyes in the centrifuged blood 248 (see FIG. 19) in expansion cavity 146 to fluoresce. The CCD array detects this fluorescent light and provides signals representative of that detection. A CPU (not shown) determines whether the CCD array 128 has detected the buffy coat layer 252 that has been sufficiently expanded by upper surface 208 in the expansion cavity 146.

If the CPU determines that the buffy coat layer 252 has not been properly detected, the next reading will be taken at the instant when the rotating rotor 108 is oriented such that expansion cavity 148 is positioned below the CCD array 128 or, in other words, the CCD array 128 is able to receive light from the area where the buffy coat layer 252 should appear on the upper surface 218 in expansion cavity 148. The CPU continues this process until the best representation of the buffy coat layer has been read. Once this occurs, the CPU can control the CCD array 128 to scan in a direction along the width of the appropriate one of the expansion cavities 146–152 to read the buffy coat layer 252 several times in that expansion cavity.

For instance, if the ideal buffy coat layer 252 appears over upper surface 218 of expansion cavity 148 as shown in FIG. 19, the CPU controls the optical reader 112 to read the thickness of that buffy coat layer several times at various positions across the width of the expansion cavity 148. This is accomplished, for example, by controlling the CCD array 128 of the optical reader 112 to receive light from the centrifuged sample in the appropriate expansion cavity at different times at which different longitudinal regions of that expansion cavity are directly below the CCD array 128. The readings of the buffy coat layer 252 are then processed to determine the count of granulocytes, lymphocytes, monocytes and platelets, and that information is provided to an operator by, for example, a display screen, printer, or both.

Although the fluid sample container 102 described above includes expansion cavities 146–152 which have upper and lower surfaces, the expansion cavities 146–152 can have alternate configurations according to the present invention. For example, the expansion cavities can each be cylindrical in shape with wider diameter end portions and a narrow diameter control portion. The wider diameter portions would essentially correspond to those sections of the expansion cavities defined by the spaces between the lower and second lower surfaces (e.g., lower surface 206 and second lower surface 214) and the inner surface of cover 134, while the narrow diameter portion would correspond to the area defined between the upper surface (e.g., upper surface 208) and the inner surface of cover 134. In this event, the inner diameter of the narrow diameter portion would be a fraction, such as ¹⁄₁₀, of the inner diameter of each of the wide diameter portions. This narrow diameter portion would have the effect of expanding the buffy coat layer in the manner described above. The fluid sample container would include, for example, four of these cylindrically shaped expansion cavities arranged in parallel or essentially in parallel to each other like expansion cavities 146–152, with the narrow diameter portions being at different locations with respect to the ends of the expansion cavities in fluid sample container 102. The expanded buffy coat layer would appear entirely in the narrow diameter portion of one of the cylindrically shaped expansion cavities.

Alternatively, instead of the distance between the inner surface of the cover 134 and the upper surface and lower surface of the expansion cavities defining the expansion cavities, the expansion cavities can be arranged so that their widths (i.e., their horizontal dimensions in FIG. 6) vary to achieve the same buffy coat layer expansion effect The fluid sample container would include, for example, four of these expansion cavities arranged in parallel or essentially in parallel to each other like expansion cavities 146–152, with the narrow width portions being at different locations with respect to the ends of the expansion cavities in fluid sample container 102. The expanded buffy coat layer would appear entirely in the narrow width portion of one of the cylindrically shaped expansion cavities.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A container for carrying a fluid sample therein, and being adaptable for use with a centrifuge which separates components of the fluid sample by density into component layers, the container comprising:

a fill well section defining at least one fill well therein, adaptable to receive the fluid sample;

a cavity section, defining a plurality of fluid expansion cavities therein, such that each of the fluid expansion cavities is adaptable to receive a portion of the fluid sample therein, and includes a respective fluid receiving area having a first cross-sectional area and a respective fluid expansion area viewable from outside the container and having a second cross-sectional area smaller than the first cross-sectional area, the fluid expansion areas each expanding a viewable surface of at least one of the component layers of its respective portion of the fluid sample when the fluid sample carried in the container is centrifuged, and the fluid expansion areas of at least two of the fluid expansion cavities are disposed at different distances from a respective end of their respective fluid expansion cavity; and a channel section, defining a channel system which provides communication between said at least one fill well and the fluid expansion cavities.

2. A container as claimed in claim 1, wherein the cavity section further comprises:

a float cavity section defining a float cavity in communication with the channel system and being adaptable for receiving therein a portion of the fluid sample which has passed through the channel system.

3. A container as claimed in claim 2, further comprising:

a float, disposed in the float cavity, and being adaptable to move in the float cavity as influenced by the portion of the fluid being received in the float cavity, such that the float becomes suspended at a location in the portion of the fluid sample received in the float cavity governed by the density of the float in relation to the densities of the fluid components.

4. A container as claimed in claim 1, wherein:

the channel section defines a portion of the channel system as a plurality of channel sections sequentially in communication with each other and extending in angular directions with respect to each other.

5. A container as claimed in claim 1, wherein:

the channel section further defines a channel distribution cavity which provides communication between the channel system and the plurality of fluid expansion cavities, and which includes a ramp area adaptable to temporarily impede flow of the fluid sample from the channel distribution cavity into the plurality of fluid expansion cavities.

6. A container as claimed in claim 1, further comprising:

a pellet, disposed in the channel system, and including a material which mixes with the fluid sample when the fluid sample flows through the channel system.

7. A container as claimed in claim 1, wherein:

the fluid sample is a blood sample; and the fluid expansion area of at least one of the fluid expansion cavities expands a viewable surface of the component layers of the buffy coat region of its respective portion of the blood sample which is formed when the blood sample carried in the container is centrifuged.

8. A container as claimed in claim 1, wherein:

each of the fluid expansion cavities has substantially the same volume.

9. A container as claimed in claim 1, wherein:

each of fluid expansion cavities extend along a first direction of the container, and are disposed in the cavity section in succession in a direction traverse to the first direction.

10. A container as claimed in claim 1, wherein:

the fluid expansion areas of each of the fluid expansion cavities are substantially the same volume.

11. A container as claimed in claim 1, wherein:

in at least one of the fluid expansion cavities, the second cross-sectional area of the fluid expansion area is substantially $1/10$th the magnitude of the first cross-sectional area of the fluid receiving area.

12. A container as claimed in claim 1, wherein:

the fluid expansion area of at least one of the fluid expansion cavities communicates with the channel section by way of its respective fluid receiving area.

13. A container for carrying a fluid sample therein, and being adaptable for use with a centrifuge which separates components of the fluid sample by density into component layers, the container comprising:

a fill well section defining at least one fill well therein, adaptable to receive the fluid sample;

a cavity section, defining a plurality of fluid expansion cavities therein, such that each of the fluid expansion cavities is adaptable to receive a portion of the fluid sample therein, and includes a fluid receiving area having a first cross-sectional area and a fluid expansion area viewable from outside the container and having a second cross-sectional area smaller than the first cross-sectional area, the fluid expansion areas each expanding a viewable surface of at least one of the component layers of its respective portion of the fluid sample when the fluid sample carried in the container is centrifuged;

a channel section, defining a channel system which provides communication between said at least one fill well and the fluid expansion cavities; and in at least one of the fluid expansion cavities, the second cross-sectional area of the fluid expansion area is substantially $1/10$th the magnitude of the first cross-sectional area of the fluid receiving area.

* * * * *